United States Patent [19]

Yorioka

[11] Patent Number: 5,018,726
[45] Date of Patent: May 28, 1991

[54] METHOD AND APPARATUS FOR DETERMINING ANAEROBIC CAPACITY

[76] Inventor: Gerald N. Yorioka, 15109 - 30th Drive S.E., Mill Creek, Wash. 98012

[21] Appl. No.: 391,124

[22] Filed: Aug. 9, 1989

[51] Int. Cl.$^5$ .......................................... A63B 21/005
[52] U.S. Cl. ............................ 272/129; 272/DIG. 6; 364/413.02; 73/379
[58] Field of Search ...................................... 272/69–73, 272/129, 130, DIG. 6; 128/25 R, 689; 73/379–381; 364/413.02, 413.04, 556

[56] References Cited

U.S. PATENT DOCUMENTS

| | | |
|---|---|---|
| 3,511,097 | 5/1970 | Corwin . |
| 3,845,756 | 11/1974 | Olsson . |
| 4,060,239 | 11/1977 | Pfeiderer et al. . |
| 4,112,928 | 9/1978 | Putsch . |
| 4,244,021 | 1/1981 | Chiles, III . |
| 4,326,539 | 4/1982 | Obermajer .................. 364/413.02 X |
| 4,358,105 | 11/1982 | Sweeney, Jr. . |
| 4,443,008 | 4/1984 | Shimano . |
| 4,566,461 | 1/1986 | Lubell et al. .................... 128/689 X |
| 4,709,917 | 12/1987 | Yang . |
| 4,790,528 | 12/1988 | Nakao et al. .......................... 272/73 |
| 4,882,677 | 11/1989 | Curran ................................. 73/379 X |
| 4,884,445 | 12/1989 | Sadoff et al. ..................... 272/130 X |
| 4,911,427 | 3/1990 | Matsumoto et al. .................. 272/73 |

Primary Examiner—Richard J. Apley
Assistant Examiner—Joe H. Cheng
Attorney, Agent, or Firm—Christensen, O'Connor, Johnson & Kindness

[57] ABSTRACT

A method and apparatus for defining and determining a value for an anaerobic capacity parameter is disclosed. The anaerobic capacity parameter is defined as the time required to completely deplete the subject's anaerobic capacity given maximum mechanical exertion by the subject under controlled conditions. A value for the anaerobic capacity parameter for a subject is generated via a testing system. The testing system includes an exercise device (12), a power characteristic sensor (14), and a processing unit (16). The exercise device (12) includes a movable component, the movement of which can represent a measurement of distance. The exercise device creates a load on the subject. The power characteristic sensor (14) is used to sense the movement of the movable component and the load imposed on the subject. Power characteristic data, e.g., movement and load data, are generated by the power characteristic sensor. The processing unit (16) is connected to the power characteristic sensor (14) such that power characteristic data and control signals are transferred therebetween. The improvement in the testing system is the inclusion of a main control program in the processing unit (16). The main control program controls the recording of power characteristic data over a test period. A set of power values indicative of the power required to move the movable component is derived from the power characteristic data. An anaerobic capacity value is determined by analyzing the logarithmic decay of the derived power values. The time to completely deplete a logarithmic function approximating the derived power values is the anaerobic capacity value. Values for parameters such as will power, total power, and power potential are also derived from the analysis.

12 Claims, 4 Drawing Sheets

*2 SECOND INTERVALS*

| TIME | POWER | % MAX | RPM |
|------|-------|-------|-------|
| 2 | 1.42 | 94 | 188.6 |
| 4 | 1.11 | 74 | 147.6 |
| 6 | 0.98 | 65 | 131.2 |
| 8 | 0.90 | 60 | 120.2 |
| 10 | 0.82 | 55 | 109.3 |
| 12 | 0.80 | 53 | 106.6 |
| 14 | 0.74 | 49 | 98.4 |
| 16 | 0.72 | 48 | 95.6 |
| 18 | 0.74 | 49 | 98.4 |
| 20 | 0.70 | 46 | 92.9 |
| 22 | 0.64 | 42 | 84.7 |
| 24 | 0.64 | 42 | 84.7 |
| 26 | 0.59 | 40 | 79.2 |
| 28 | 0.59 | 40 | 79.2 |
| 30 | 0.55 | 37 | 73.8 |
| 32 | 0.53 | 35 | 71.1 |
| 34 | 0.51 | 34 | 68.3 |
| 36 | 0.49 | 33 | 65.6 |
| 38 | 0.45 | 30 | 60.1 |
| 40 | 0.45 | 30 | 60.1 |
| 42 | 0.45 | 30 | 60.1 |
| 44 | 0.43 | 29 | 57.4 |
| 46 | 0.41 | 27 | 54.7 |
| 48 | 0.41 | 27 | 54.7 |
| 50 | 0.41 | 27 | 54.7 |
| 52 | 0.37 | 25 | 49.2 |
| 54 | 0.37 | 25 | 49.2 |
| 56 | 0.37 | 25 | 49.2 |
| 58 | 0.37 | 25 | 49.2 |
| 60 | 0.37 | 25 | 49.2 |

FIG.3.

METHOD AND APPARATUS FOR DETERMINING ANAEROBIC CAPACITY

TECHNICAL AREA

This invention relates to a method and apparatus for determining the power output of a human subject, and, more particularly, for defining and determining the anaerobic capacity of a human subject.

BACKGROUND OF THE INVENTION

Physical examinations are required or desirable in a variety of situations. In the past, complete physical examinations have been generally geared towards disease detection rather than towards evaluating the functional, e.g., aerobic and anaerobic, capacity of the human body. To some people, particularly those in low disease risk groups, the fact that no disease is found during an examination may not be a motivating enough reward to take a physical examination. It is believed that meaningful tests of functional capacity as part of a physical examination may encourage more people to take physical examinations because the results of such tests are of practical value that can be used to set functional capacity goals. Thus, the physical examination becomes a vehicle for improvement as well as a disease detection procedure.

Human functional capacity tests have been generally oriented to aerobic capacity with little attention or emphasis having been given to the anaerobic capacity other than as it relates to aerobic activity. Aerobic and anaerobic capacity reflect the condition of a subject's aerobic and anaerobic metabolisms, respectively. Aerobic metabolism refers to the body's method of producing energy by a process requiring oxygen. Whenever the available amount of rate of oxygen-based energy is exceeded, an anaerobic state is entered in which energy is produced by a process that does not require oxygen, but may result in oxygen debt. Thus, aerobic and anaerobic metabolism are related but separate functions. Capacity in this sense refers to some measure of the metabolism's overall ability to produce energy. For example, a time value indicative of the time it takes under given conditions to deplete the subject's energy production to zero is one measure of capacity.

It is of value to distinguish the aerobic metabolism energy sources from anaerobic metabolism energy sources. Muscles contract from phosphorylation of adenine triphosphate (ATP). Metabolic energy sources replenish the ATP when sustained or repeated muscle contractions occur. Aerobic oxidative phosphorylation provides ATP at a steady rate until the energy reserves of glycogen or fatty acids are depleted. At this point, or just prior to this point, anaerobic metabolism begins. Also, anaerobic metabolism is also called upon when higher levels of mechanical work are required. The anaerbic metabolism sources of ATP are less efficient, require more caloric energy to produce ATP, are depleted sooner, and produce an oxygen debt.

Muscle contraction can also be viewed in terms of the behavior of the nerve-muscle combination called the motor unit. There are three types of motor units: I, IIA, and IIB. Type I motor units draw energy from aerobic metabolism. Type IIA motor units draw energy from aerobic and anaerobic lactate metabolism. Type IIB motor units draw energy aerobic and anaerobic lactate metabolism, plus creatinine phosphatase enzyme metabolism. Type IIB motor units are brought into action only when a higher force of muscle contraction takes place. Training of motor units is specific since only those units trained will respond. With respect to performance, the creatinine phosphate production of ATP is brief and is believed to deplete in 10–15 seconds under maxiumum loads. The lactate system is believed to deplete in 5–15 minutes under maximum loads.

Interest in aerobic exercise and fitness has naturally evolved from interest in cardiac output evaluations since a decrease in cardiac output can reflect coronary artery deterioration. If the cardiorespiratory and mechanical efficiency of a subject remains unchanged, the oxygen consumption of the subject during exercise relates directly to the cardiac output. To test the aerobic capacity of a subject, a standard treadmill stress test is often used. The aerobic work performed during the treadmill test is directly related to oxygen consumption and thus to cardiac output. The aerobic exercise level achieved and measured on the test is commonly used as the basis for estimating cardiac output. Using such tests, oxygen consumption and cardiac output are indirectly measured by measuring the aerobic treadmill performance. Such tests do not generally measure anaerobic parameters.

At least two categories of anaerobic metabolism are known and are important in their own right. These are anaerobic peak power output and anaerobic capacity. Anaerobic test systems that provide a method for testing power and capacity have been devised. A common test for estimating anaerobic power is a 30-second bicycle ergometer test. In this test the subject pedals an exercise bicycle as fast as possible with a measured fixed load for 30 seconds. Values for the RPM of the bicycle pedal during the test are combined with a value for the load imposed on the subject by the exercise device to produce a set of derived power values over the test period. The power values calculated for each 5-second subinterval are averaged over the 30-second test period to produce an average power value. In one test, an anaerobic capacity parameter is defined as the average power value for a test period. In the same test, a peak power parameter is defined as the highest power value for a five-second subinterval that is measured during the test period. Unfortunately, this test protocol has a number of disadvantages. First, the definition of the anaerobic capacity parameter does not account for varying energy depletion or power decay rates of the physiological process that actually occurs as the body progresses through various exercise states, specifically through anaerobic energy producing states. Secondly, the peak power value produced by this test protocol may be inaccurate and, thus, misleading, since considerable undetected changes in power output may occur during a 5-second sampling subinterval.

Comparing an aerobic treadmill test and an anaerobic bicycle test illustrates that the former stems from interest in the work potential of the heart, e.g., cardiac performance, while the latter originates from interest in the work potential of the body, e.g., mechanical performance. It is desirable to provide an accurate measure of anaerobic capacity as an indication of the subject's capacity to produce energy via anaerobic metabolism as well as an indication of the state of the specific muscle types that draw energy from anaerobic metabolism.

The mathematical model for the natural decay of total power is described as follows:

$$P_{total} = P_1 + P_2 + P_3 + \ldots P_n,$$

where each metabolic component is $P_i = e^{k_i t}$. The first approximation that assumes that one metabolic power source is dominant in the contribution of power is expressed as $P_{total} = e^{-kt}$.

By design of the present invention, the anaerobic lactate metabolism is emphasized in the production of power. By imposing a heavy load on the subject that far exceeds the subject's aerobic power capabilities, the aerobic component of the total power is minimized. By extending the length of the test well beyond the expected depletion time of the aerobic creatinine phosphate metabolism, the dominant component of the power decay that is measured represents the power decay of the anaerobic lactate metabolism.

The present invention provides a definition of an anaerobic capacity parameter that is related to the subject's capacity to produce energy via anaerobic metabolism. The invention also provides a method and apparatus that provide a quick and meaningful assessment of anaerobic exercise parameters. These parameters include anaerobic capacity (anaerobic endurance time), will power, total work, peak power, potential power, stamina, average power, and fade. When compared to an isolated aerobic view of human activity, the exercise parameters of the present invention have many practical applications, e.g., monitoring daily activities, special work demands, athletic achievement, and rehabilitation. The present invention provides a simple, brief, noninvasive method and apparatus for determining the anaerobic capacity of an individual.

SUMMARY OF THE INVENTION

In accordance with this invention, an improved method and apparatus for defining and determining values for anaerobic capacity and related exercise parameters is provided. The anaerobic capacity parameter is defined as an approximation of the time it takes for a subject's anaerobic power output to be nearly completely depleted in the instance where the subject is exerting maximum effort. It has been found that anaerobic power output decays in a natural logarithmic fashion. Thus, the anaerobic capacity parameter is further defined as the time interval over which a logarithmic function that approximates the subject's actual anaerobic power output is reduced to zero.

In order to evaluate a given subject's anaerobic capacity, a value for the anaerobic capacity parameter is calculated for a testing session. The testing session requires the subject to exert maximum mechanical effort during a test period and under controlled conditions. The power output over the test period is derived from power characteristic data and analyzed to produce a set of values for a number of exercise parameters.

The testing apparatus includes an exercise device, a power characteristic sensor, and a processing unit. The exercise device, which may be an exercise bicycle, a rowing machine, etc., includes a movable component. The movement of the movable component corresponds to a measure of distance. For example, on an exercise bicycle, the movable component is a wheel and the revolutions of the wheel represent a measurable distance. The power characteristic sensor senses the movement of the movable component, e.g., the revolutions of a wheel, and the load, if any, that is provided by the component. The power characteristic sensor generates power characteristic data. The data includes distance and load data. Alternatively, the data is combined by the sensor to produce power data for discrete time periods. The processing unit is connected to the sensor such that data and control signals can be transferred therebetween. The improvement includes a main control program coupled to the processing unit. The main control program receives the power characteristic data that is received by the processing unit from the sensor. The data is used to derive a set of power values indicative of the subject's power output over the test period. The main control program uses the set of derived power values to determine an anaerobic capacity value for the test period. The anaerobic capacity value represents an approximation of the time it would take to completely deplete the subject's anaerobic power output based on the test period performance.

In accordance with further aspects of the present invention, the main control program derives power values over subintervals of the test period. A value for the anaerobic capacity parameter is determined by analyzing a logarithmic power decay function that approximates the logarithmic decay of the derived power values. An ideal power decay function may be used to approximate the derived power values. The ideal power decay function is the function that describes the straight line that runs through the semilogarithmic plot of the derived power values at the first-half subinterval and second-half subinterval of the test period. The anaerobic capacity value is the sum of five half-lives of the ideal power decay function. Alternatively, a logarithmic function that estimates a best-fit line for the semilogarithmic plot of the derived power values is used to approximate the derived power values. The alternative anaerobic capacity value is also the sum of five half-lives of the best-fit line function.

In accordance with other aspects of the present invention, the subintervals of the test period are less than one second. The derived power value for each subinterval represents a measurement of instantaneous power for the subinterval.

In accordance with still further aspects of the present invention, the main control program also determines a value for a will power exercise parameter. The will power parameter is defined as the lack of deviation of the derived power values from a smooth power drop. The smooth power may be represented by the ideal power decay function or the best-fit line function for a given set of derived power values. A deviance value is determined for each subinterval as the difference between the derived power value and the smooth power function value at each subinterval time. The total deviance is the sum of the absolute values of the subinterval deviance values. The will power value is calculated as 100 percent minus the percentage of the total area under the smooth power drop, e.g., the total work output, that is represented by the total deviance value.

In accordance with still other aspects of the present invention, exercise parameters indicative of total work, peak power, potential power, stamina, average power, and fade are defined and specific values for the parameters are calculated by the main control program for a given set of test data.

BRIEF DESCRIPTION OF THE DRAWINGS

The foregoing and other features and advantages of this invention will become more readily appreciated as the same becomes better understood by reference to the following description of a preferred embodiment of the invention when taken in conjunction with the accompanying figures wherein:

FIG. 3 is a table including a sample set of derived power values; and

DETAILED DESCRIPTION OF THE EMBODIMENTS

The present invention provides a method and apparatus for analyzing the anaerobic power output of a subject. The invention defines an anaerobic capacity parameter and provides an improved method and apparatus for calculating an anaerobic capacity value for a subject based on the results of a testing session. It has been found that anaerobic power output decays in a natural logarithmic fashion. Thus, the present method and apparatus analyze the subject's anaerobic power output in terms of natural logarithmic decay. This analysis produces exercise parameter values that closely correspond to the subject's anaerobic metabolism.

Figure 1:
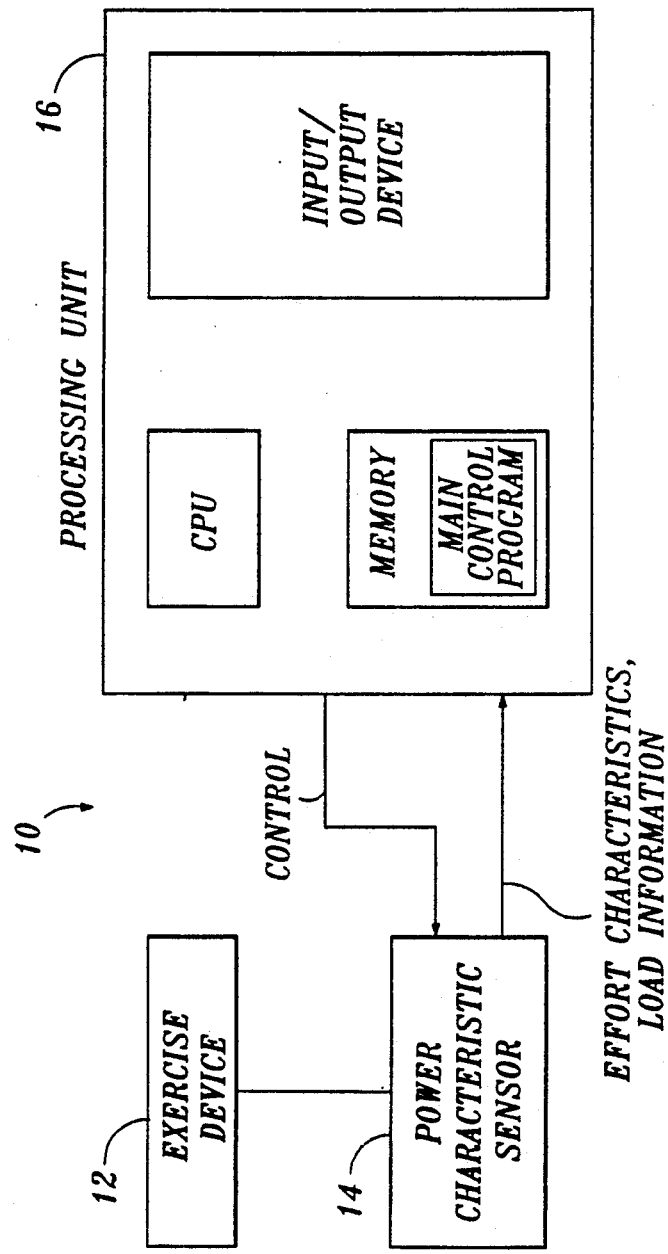
FIG. 1 is a block diagram of an exercise testing system formed in accordance with the present invention.

With reference to FIG. 1, the testing system 10 includes exercise device 12, power characteristic sensor 14, and processing unit 16. The exercise device 12 is a device that a subject can utilize to exert mechanical effort. Suitable exercise devices include exercise bicycles, rowing machines, treadmills, etc. The exercise device must be configured so that the subject's effort is reflected in some operation of the device. For example, on an exercise bicycle, the revolutions of the bicycle wheel may be measured over an interval of time to produce a measurement of revolutions per minute (RPM). Similarly, on a rowing machine, the number of strokes per minute can be measured to provide a measure of distance over time. The bicycle wheel and rowing machine handles are referred to as the devices' movable components.

Such exercise devices produce at least a nominal load on the subject during use. Preferably, an adjustable load may be placed on the subject's use of the exercise device. An adjustable load is obtained by placing a load on the movable component via a variable loading component. An example of a loading component on an exercise bicycle is a friction belt that can be tightened against the wheel using a mechanical tightening mechanism. As another example, an electromechanical loading component includes a sprocket, a belt connecting the sprocket with the flywheel of the exercise bicycle to adjust the load on the flywheel, and an alternator generator or electromagnet for providing variable resistance to the sprocket in response to an input signal.

The power characteristic sensor 14 is a device for sensing the operation of the exercise device 12. Specifically, the sensor monitors the movement of the movable component, e.g., distance, and the load thereon and generates data indicative of the sensed characteristics. For example, an ergometer is a commercially available sensor for use with an exercise bicycle. An ergometer generally detects the rotation of the bicycle wheel and produces a value or signal indicative of the wheel's RPM. A signal indicative of a value for the load introduced on the moveable component by the loading component may be obtained from the electromagnetic-mechanical loading component.

The processing unit 16 is connected to the power characteristic sensor 14 in order to communicate loading control signals to the sensor and to receive the movement and load data from the sensor. In one preferred embodiment, the processing unit is made up of a microcomputer including a central processing unit (CPU), input and output devices, and a memory. The input and output devices in the processing unit 16 may be a conventional keyboard and screen display, respectively. In one actual embodiment, the output device includes a printer for producing a hard copy of the test results for the subject's records.

The memory includes a main control program 18. As the main control program is executed by the CPU, it controls the collection of data from the power characteristic sensor over a period of time, and the generation and display of values for a number of exercise parameters. Each exercise parameter value is calculated by analyzing the collected data in terms including the natural logarithmic power decay.

A testing session in accordance with the present invention is illustrated using a testing system including an exercise bicycle as the exercise device 12. In one actual embodiment, a loading component such as the alternator controlled electromechanical system described above is used. An ergometer that outputs signals indicative of the wheel RPM is utilized. The ergometer and the loading component comprise the power characteristic sensor 14. A microcomputer is connected to the ergometer and the loading system via a standard data bus.

Figure 2:
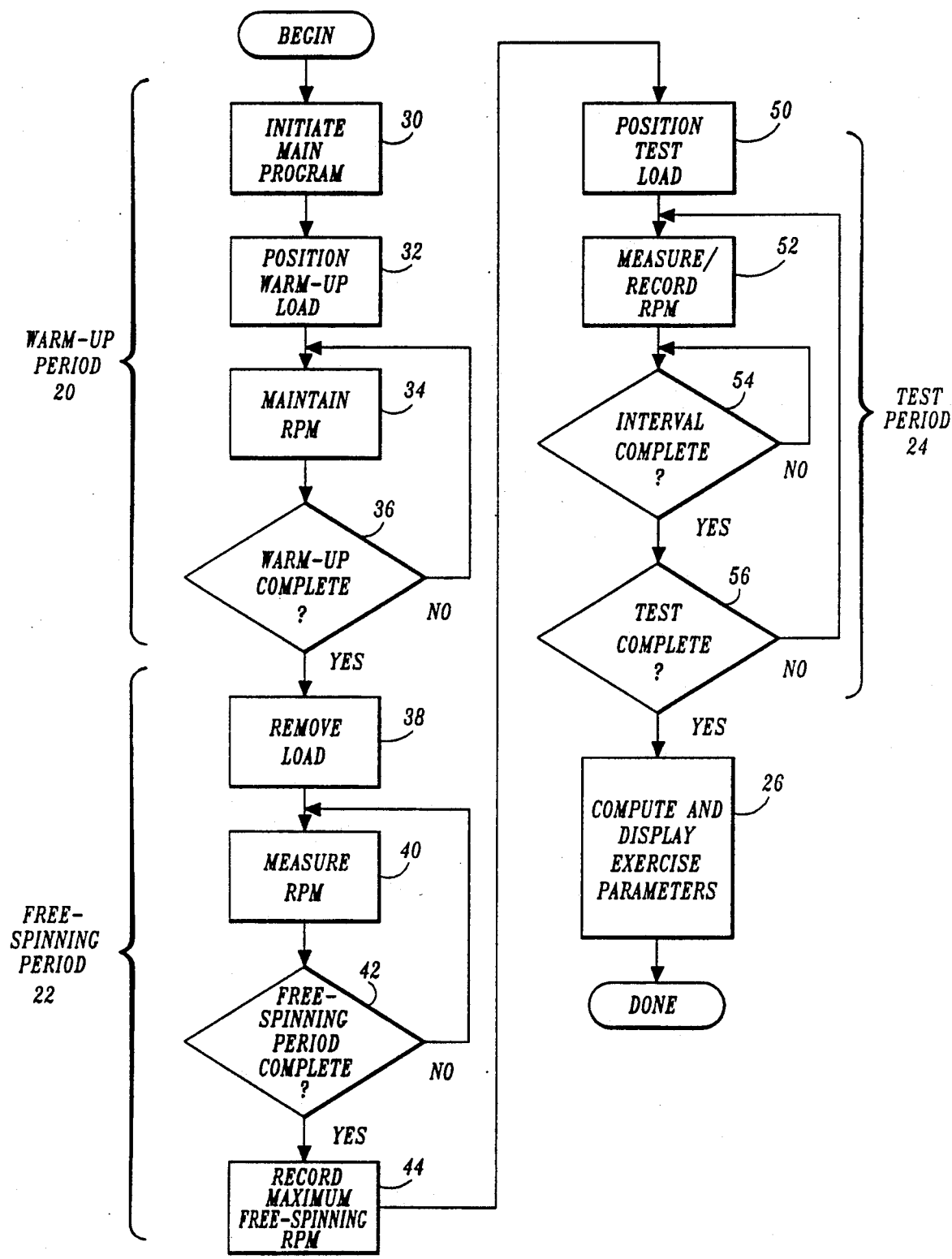
FIG. 2 is a flow diagram of a testing procedure created in accordance with the present invention and carried out by the processing unit illustrated in FIG. 1.

With reference to FIG. 2, a testing session comprises a warm-up period 20, a free-spinning period 22, and a test period 24. After the test period, values for the various exercise parameter are calculated and displayed at block 26.

During the warm-up period 20, the main control program is initiated at block 30. A light load is placed on the bicycle wheel at block 32. The subject is required to maintain a relatively low level of RPM at block 34. The combined load, RPM and length of the warm-up period are adequate to raise the subject's cardiovascular system to an appropriate exercise level. In one actual embodiment, the warm-up load is 10 Newtons (=1 Kilopon) and the subject maintains a speed of approximately 50 RPM. At this load and rate, a warm-up period of two minutes is suitable. At block 36, the processing unit checks a timer, e.g., a CPU clock component, to determine whether the warm-up period has expired.

After the warm-up period, the load is removed at block 38 and the subject spins the bicycle freely. The free-spinning period 22 is long enough to allow the subject to attain a maximum RPM. In one actual embodiment, the free-spinning period is five seconds. As the subject spins freely, the processing unit receives RPM measurements from the ergometer at block 40. These measurements are stored by the main control program. At block 42, the processing unit checks a timer to determine whether the free-spinning period has expired. After the free-spinning period has expired, the maximum free-spinning RPM is determined by the main control program from the collected RPM data and recorded at block 44. This value is representative of the subject's maximum attainable RPM.

After the free-spinning period, the test period 24 begins. During the test period, the subject exerts a maximal all-out effort in pedaling the bicycle. Based on empirical studies, a one-minute test period is preferable for testing anaerobic capacity. In a testing system including an automatic loading component, the main control program transmits control signals to the loading component to thereby cause a predetermined load to be instantaneously placed on the bicycle wheel at block 50. Alternatively, the load may be manually positioned on the bicycle wheel. No matter how the load is positioned, it is preferable that the positioning be done relatively instantaneously. In one actual embodiment, the load is calculated according to the subject's weight. In this embodiment, a load in the range of 0.5-1.0 Newtons/kg. body weight is applied. Alternatively an equivalent load based on lean body mass, muscle mass, or ideal weight is applied. The load data is recorded by the main control program.

The main control program begins sampling the ergometer output at block 52. The sampling is preferably done at the expiration of relatively short time intervals, referred to as subintervals, as checked at block 54. In one actual embodiment, the ergometer output is sampled once every half second. After each sampling subinterval, at block 56, the main control program checks a timer to determine whether the full test period has expired. If the full test period has not expired, the ergometer sampling is repeated at block 52.

Once the test period has expired at block 56, the main control program indicates to the operator that the test is complete. The RPM and load data are then analyzed and the test results output to the operator at block 60. Initially, a power value for each half second subinterval is derived by multiplying the RPM measurement for each subinterval by the load value. The results of the calculation is a set of derived power values. In the present embodiment, velocity data, e.g., RPM data is received directly from the power characteristic sensor. In an alternative system, wherein the movement data received from the power characteristic sensor is distance data, the main control program calculates a velocity value for each subinterval by multiplying the distance over the subinterval by the subinterval length. Those velocity values are used to derive the power values.

As noted above, it has been found that anaerobic power output decays in a logarithmic fashion. Thus, in order to calculate an anaerobic capacity value, a logarithmic analysis is done of the derived power values. With reference to FIG. 3, a sample set of derived power values over a test period is set out. The values are represented as plot L on a semilogarithmic graph in FIG. 4. For ease of illustration, the derived power values for each two-second subinterval rather than for each half-second subinterval are plotted.

When a logarithmically decaying function is plotted on a semilogarithmic graph, the half-life of the function will be constant. In one embodiment of the present invention, the anaerobic capacity parameter is defined as the sum of five half-lives of a logarithmic power decay function that approximates the derived power output over the test period. Five half-lives represent approximately 97% depletion of the anaerobic capacity of the subject. The use of five half-lives for a depletion point represents a practical total depletion point since the total depletion time is theoretically infinite.

Figure 4:
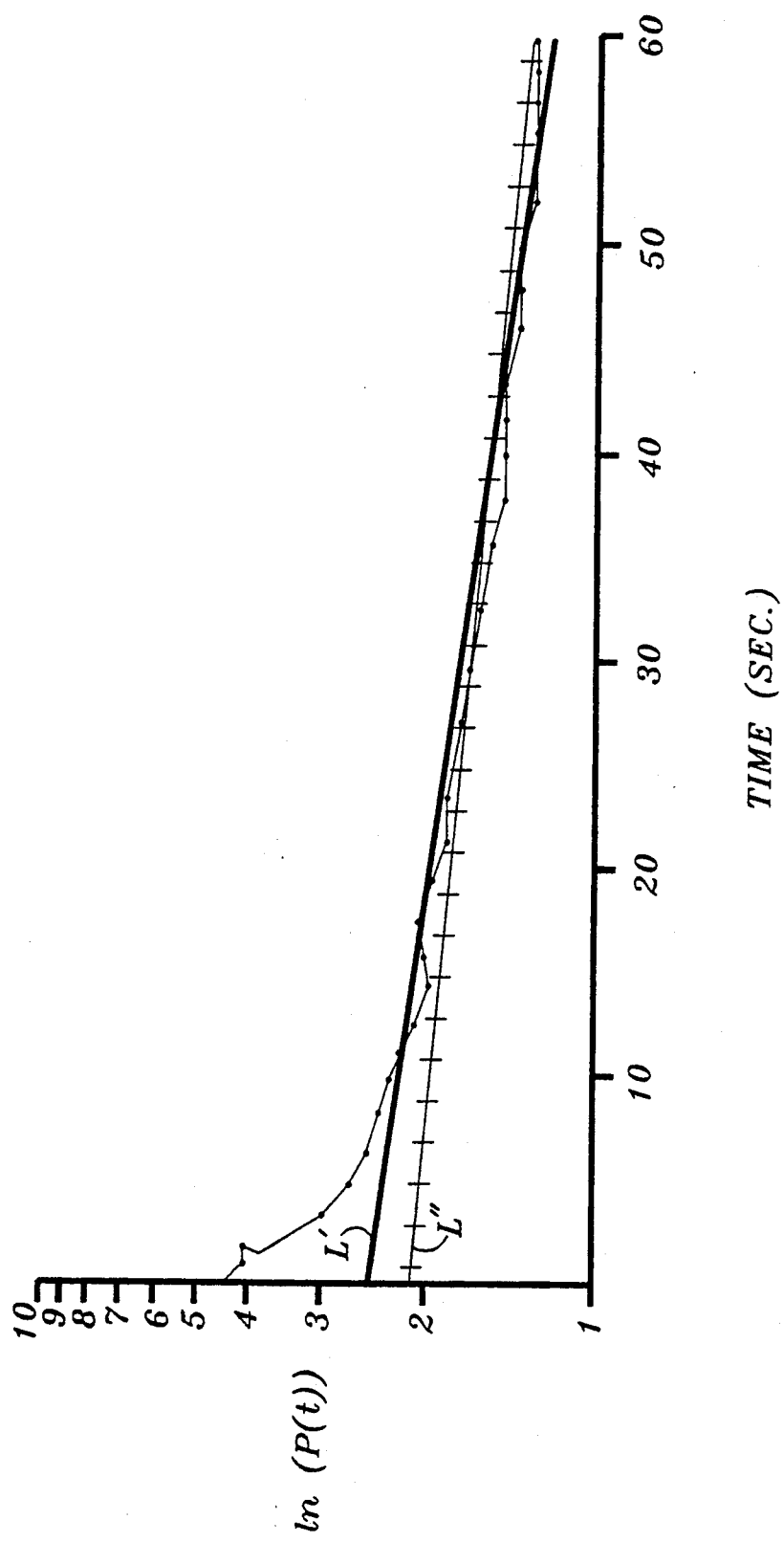
FIG. 4 is a graphic depiction of the sample set of derived power values on a semilogarithmic graph, including plots for a related best-fit line function and an ideal power decay function.

In order to calculate an anaerobic capacity value for a given subject, a logarithmic power function approximating the derived power values is analyzed. One means for approximating the derived values is a best-fit power function overlaid on the derived power value graph. With reference to FIG. 4, an estimated best-fit line L' is overlaid on the derived power value graph. The equation for the best-fit line is $L'=e^{-kt}$, with k representing the slope of the line. In the example, the slope k for L' is approximately $-0.015$ HP/sec. One half-life for the power decay is found by determining the relationship between a first time t' and a second time t'' at the point such that $P(t'')=\frac{1}{2}P(t')$ and the difference $(t''-t')$ is equal to one power half-life. In the present example, one power half-life is equal to approximately 72 seconds. Thus, five power half-lives, or the anaerobic capacity value, is approximately 360 seconds or 6 minutes. Thus, the subject would completely diminish his/her ability to produce energy via anaerobic metabolism if maximum mechanical effort were exerted for 6 minutes under the given test conditions. This anaerobic capacity value is used as a reference for future tests of the same subject. As the subject is able to maintain a more constant and higher rate of power output over the test period, this value will increase accordingly.

An alternative straightline power function for approximating the derived power values is an ideal power decay function. The ideal power decay function is represented by the equation $L''=e^{-kt}$. The constant k is the slope of the natural logarithm of the power line L'' between the first half and the second half of the test period. The slope k for the sample data is equal to approximately $-0.0097$ HP/sec. With reference again to FIG. 4, the hashed line L'' illustrates the ideal power decay function for the present example. The anaerobic capacity value alternatively is calculated as five-half lives of the ideal power decay function.

Another exercise parameter calculated by the main control program is will power percentage. The will power value for a test period represents the lack of deviation of the subject's power output from a smooth power output, e.g., one that decays in a consistent manner. A high will power percentage is an indication that the subject's power output over the test period was not erratic. The will power parameter is defined as 100% minus the area between the plot of the derived power data and the smooth power decay plot divided by the area under the smooth power decay plot, e.g., the total work. In one actual embodiment, the ideal power decay function is used to represent the smooth decay function. A deviation value for each subinterval is the difference between the derived power value and the ideal power times the subinterval time. A total deviation value is the sum of the absolute values of the subinterval deviations. The total deviation value is then divided by the area under the smooth power decay plot and then subtracted from 100% to produce a will power value. In the present example, the will power percentage is approximately 82%.

A total work value is also generated by the main control program. The total work parameter is defined as the area under the derived power value graph. The power function for the best-fit line or the ideal power decay may be used to provide a simple means for estimating the area under the derived power value graph. By calculating the integral of the formula $P=e^{-kt}$, a total work value is obtained. In the present example, this value is approximately 42,750 ft-lbs.

A peak power parameter is defined as the highest derived power value for a subinterval during the power test. By sampling the RPM at very small subintervals, e.g., half-second intervals, the derived power values closely correspond to the instantaneous changes in the power output that occur over the test period. In the present example, the peak power value is 1.42 HP measured at the first two-second subinterval.

A power potential parameter is defined as the peak power value multiplied by the anaerobic capacity value (anaerobic endurance time). This parameter represents the subject's potential work output if the subject is able to maintain the peak power output over the anaerobic capacity time. In the present example, the power potential value is $9.35 \times 10^6$ ft-lbs.

Other exercise parameter values that are determined using the present invention include stamina, average power, and fade. The stamina parameter is a percentage indication of how close the subject came to maintaining the maximum unloaded RPM over the entire test period. The stamina parameter is defined as the work that would have been done if the maximum RPM was maintained with the load. The parameter is calculated as the total work during the test period divided by the product of the maximum unloaded RPM and the length of the test period. In the example, an unloaded maximum RPM of 200 was achieved during the free-spinning period. A stamina value is calculated by the main control program as approximately 43%. A stamina value of 100% is achieved when the subject is able to maintain the free-spinning period RPM throughout the test period.

The average power parameter is defined as the average of the derived power values over the test period. In the present example, the average power value is 0.648 HP.

The fade parameter is defined as the direct drop from the maximum loaded RPM to the finishing RPM. The calculation of fade using the sample derived power values produces a value of approximately 74%.

While preferred embodiments of the invention have been illustrated and described, it will be appreciated that various changes can be made therein without departing from the spirit and scope of the invention. Generally, the invention can be integrated into any testing system that includes an exercise device, the operation of which can be described in terms of power output. Additionally, the entire test system can be integrated into a single-purpose system rather than into a general purpose microcomputer.

In an alternative testing system including an exercise bicycle, the power characteristic sensor 14 includes means for sensing the position of a gear setting mechanism on the bicycle. The setting of the gears on such a bicycle correspond to the load on the wheel. The gears are manually set during the warm-up, free-spinning, and testing cycles. The power characteristic sensor provides the gear setting information to the main control program. A load value corresponding to the gear setting is generated by the main control program from gear-to-load data for the bicycle. In another alternative embodiment, a commercially available bicycle ergometer that generates RPM and load data is used. In such an ergometer, the power value output is calculated from a table of measured RPM-to-load value pairs. The RPM value and load value for each sampling interval is received by the main control program during the test period. The main control program then applies the table conversion for power values-to-load values at the appropriate test subintervals to produce a set of derived power values.

In an alternative testing system configuration, using a manually set load, the CPU obtains load information by direct operator input into the processing unit.

With respect to the methods for calculating values for the exercise parameters, it is clear that the best-fit power function and the ideal power decay function may be interchanged in the various analyses. However, for each subsequent test-retest for the same subject, the power function that was previously used to calculate a given value for an exercise parameter should be used consistently. For example, if the anaerobic capacity value is first calculated using an ideal power decay function, then the value should subsequently be calculated using an ideal power decay function approximating the current set of derived power values. Additionally, other methods for analyzing the depletion of the anaerobic power are suitable for use with this invention.

Finally, the main control program may also include modules for receiving and maintaining other pertinent patient information such as sex, weight, age, height, etc. This information is then used to produce a complete patient history in conjunction with the exercise parameter information generated by the testing system. As noted above, certain of the test parameters, such as test period load, may be selected according to patient information such as weight.

The embodiments of the invention in which an exclusive property or privilege is claimed are defined as follows:

1. In an apparatus for measuring exercise parameters comprising: an exercise device including a movable component that creates a load on a user of the exercise device; sensor means connected to the exercise device for sensing the movement of the movable component, for quantitating the load created by the movable component, and for producing related power characteristic data; and a processing unit connected to the sensor means for receiving the power characteristic data, the improvement comprising:
   main control means coupled to the processing unit for:
   (a) continuously receiving the power characteristic data over a test period;
   (b) continuously deriving a set of power values over said test period based on the received power characteristic data, said power values being indicative of the power required to move the movable component during said test period; and
   (c) determining an anaerobic capacity value from said set of derived power values which represents to the time required to completely deplete a user's anaerobic capacity when the user exerts maximum mechanical effort, by analyzing the logarithmic power depletion of said derived power values over said test period.

2. The improved apparatus as claimed in claim 1, wherein said main control means derives said power values over subintervals of less than one second over said test period.

3. The improved apparatus as claimed in claim 2, wherein said anaerobic capacity value is determined as the sum of five half-lives of said logarithmic power depletion.

4. The improved apparatus as claimed in claim 3, wherein said logarithmic power depletion is estimated by a best-fit logarithmic function through said set of derived power values.

5. The improved apparatus as claimed in claim 3, wherein said logarithmic power depletion is estimated by an ideal power decay function through said set of derived power values.

6. The improved apparatus as claimed in claim 1, wherein said main control means further calculates a total work value by summing said derived power values over said test period.

7. The improved apparatus as claimed in claim 6, wherein said main control means further determines a will power value, said value being determined by calculating 100 minus the percentage of the sum of the absolute total work deviation from an ideal power decay function over said test period.

8. The improved apparatus as claimed in claim 6, wherein said main control means also:
   (a) receives distance data during a pretest period;
   (b) derives a pretest maximum velocity value for said pretest period from said distance data;
   (c) determines a maximum unloaded work value equal to the product of said pretest maximum velocity value and the length of said test period; and,
   (d) determines a stamina parameter by dividing said total work value by said maximum unloaded work value.

9. The improved apparatus as claimed in claim 1, wherein said main control means further generates a power potential value by determining a maximum power value from said set of derived power values and by multiplying said anaerobic capacity value by said maximum power value to produce said power potential value.

10. The improved apparatus as claimed in claim 1, wherein said power characteristic data comprises distance and load data.

11. The improved apparatus as claimed in claim 1, wherein said power characteristic data comprises power data generated by the sensor means from the sensed movement and load of the exercise device.

12. A method for measuring exercise parameters carried out in conjunction with the operation of an exercise apparatus, said apparatus comprising: an exercise device including a movable component that creates a load on a user of the exercise device; sensor means connected to the exercise device for sensing the movement of the movable component and the load created by the movable component and for producing related power characteristic data; and a processing unit connected to the sensor means for receiving the power characteristic data, the method comprising:
   (a) continuously receiving the power characteristic data over a test period;
   (b) continuously deriving a set of power values over said test period based on the received power characteristic data, said power values being indicative of the power required to move the movable component during said test period; and
   (c) determining an anaerobic capacity value from said set of derived power values which, represents to the time required to completely deplete a user's anaerobic capacity when the user exerts maximum mechanical effort, by analyzing the logarithmic power depletion of said derived power values over said test period.

* * * * *